(12) United States Patent
Nishida (10) Patent No.: US 9,880,087 B2
(45) Date of Patent: Jan. 30, 2018

(54) REMAINING SERVICE LIFE EVALUATION METHOD FOR METAL PIPE SUFFERING FROM CREEP DAMAGE

(71) Applicant: THE CHUGOKU ELECTRIC POWER CO., INC., Hiroshima (JP)

(72) Inventor: Hidetaka Nishida, Hiroshima (JP)

(73) Assignee: THE CHUGOKU ELECTRIC POWER CO., INC., Hiroshima (JP)

( * ) Notice: Subject to any disclaimer, the term of this patent is extended or adjusted under 35 U.S.C. 154(b) by 72 days.

(21) Appl. No.: 15/023,361

(22) PCT Filed: Jan. 24, 2014

(86) PCT No.: PCT/JP2014/051495
§ 371 (c)(1),
(2) Date: Mar. 18, 2016

(87) PCT Pub. No.: WO2015/111184
PCT Pub. Date: Jul. 30, 2015

(65) Prior Publication Data
US 2016/0258860 A1    Sep. 8, 2016

(51) Int. Cl.
*G01N 17/00* (2006.01)
*G01N 3/12* (2006.01)

(52) U.S. Cl.
CPC ............ *G01N 17/006* (2013.01); *G01N 3/12* (2013.01); *G01N 17/008* (2013.01); *G01N 2203/0071* (2013.01)

(58) Field of Classification Search
CPC ............ G01N 3/00; G01N 3/12; G01N 17/00; G01N 17/006; G01N 17/008; G01N 2203/0071; G01N 33/20
See application file for complete search history.

(56) References Cited

U.S. PATENT DOCUMENTS 2,928,726 A * 3/1960 Oberly .................. G01N 17/00
422/53
5,447,057 A   9/1995 Shaw et al.
2004/0035216 A1* 2/2004 Morrison ............. E21B 17/015
73/800

FOREIGN PATENT DOCUMENTS

| JP | 3976938 B2 | 9/2007 |
| JP | 2010-014600 A | 1/2010 |
| JP | 2012-189476 A | 10/2012 |
| JP | 2013-148476 A | 8/2013 |

(Continued)

OTHER PUBLICATIONS

International Preliminary Report on Patentability and Translation of Written Opinion issued in corresponding International Application No. PCT/JP2014/051495 dated Aug. 4, 2016, (5 pages).

(Continued)

*Primary Examiner* — Nguyen Ha
(74) *Attorney, Agent, or Firm* — Osha Liang LLP (57) ABSTRACT

A remaining service life evaluation method for evaluating a remaining service life of a metal pipe suffering from creep damage on a basis of a master curve that is prepared in advance that includes wrapping a steel strip around an outer peripheral face of the metal pipe under same conditions as those during an internal pressure creep test and evaluating a remaining service life of the metal pipe on a basis of a degree of deterioration of the steel strip.

8 Claims, 4 Drawing Sheets

(56) References Cited

FOREIGN PATENT DOCUMENTS

WO 2005/124315 A1 12/2005

OTHER PUBLICATIONS

International Search Report issued in PCT/JP2014/051495 dated Apr. 8, 2014 (4 pages).
Office Action in corresponding Chinese Patent Application No. 201480052547.4 dated Nov. 17, 2017, with translation (7 pages).

* cited by examiner

REMAINING SERVICE LIFE EVALUATION METHOD FOR METAL PIPE SUFFERING FROM CREEP DAMAGE

TECHNICAL FIELD

One or more embodiments of invention relate to a remaining service life evaluation method for a metal pipe suffering from creep damage.

BACKGROUND ART

Steam is effectively used in power stations and factories as a heat source and a pressure source. Metal pipes manufactured from stainless steel or chromium steel are employed for steam distribution. Such metal pipes suffer from creep damage when steam is at high temperature and high pressure, for example, in cases where the steam temperature is several hundreds of degrees Celsius, and the steam pressure is several Mpa.

Thus, when metal pipes are large diameter pipes employed for motive steam used in turbines or the like, in cases in which, for example, the pipe has a diameter of several hundred mm, creep voids develop in the surface of the metal pipe due to creep damage, and the number and surface area of the creep voids increase with the progression of creep damage. Remaining service life evaluation methods, such as an A parameter method or an M parameter method, have been proposed that take into consideration the characteristic way in which the number and surface area of creep voids increase (see Patent Documents 1 and 2).

CITATION LIST

Patent Literature

Patent Literature 1: Japanese Patent Application Laid-Open No. 2010-14600.
Patent Literature 2: Japanese Patent No. 3976938.

SUMMARY

However, when a metal pipe is a small diameter pipe with a diameter of 100 mm or less (for example, a boiler pipe), such a small diameter pipe behaves in a different manner from the large diameter pipes mentioned above. There is, for example, a trend for creep voids to develop and increase rapidly at the end of service life of a small diameter pipe, to the point at which rupturing occurs. It is accordingly difficult to apply the same remaining service life evaluation method as that of large diameter pipes. Due to the above situation, the surface of a small diameter pipe is scraped off, and ultrasound and magnetic measurements are performed of the wall thickness and bulging. However, in this method, the surface of a small diameter pipe is scraped off, and so the wall thickness becomes thinner each time measurements are performed. As a result, the service life of the small diameter pipe is shortened by the amount scraped off.

One or more embodiments of the invention are to measure the remaining service life of a metal pipe suffering from creep damage without scraping the surface of the metal pipe.

One or more embodiments of the invention relate to a remaining service life evaluation method for evaluating remaining service life of a metal pipe, suffering from creep damage on a basis of a master curve that is prepared in advance, the master curve being prepared by performing an internal pressure creep test in a state in which a steel strip, made of a metal material having a thermal expansion coefficient and strength of the metal pipe or greater, is wrapped under tension around an outer peripheral face of a test piece made of the same material and having the same inner and outer diameters as the metal pipe, the master curve indicating a relationship between a degree of deterioration of the steel strip and a remaining service life of the metal pipe, the remaining service life evaluation method including: wrapping a steel strip around an outer peripheral face of the metal pipe under the same conditions as those during the internal pressure creep test; and evaluating a remaining service life of the metal pipe on a basis of a degree of deterioration of the steel strip.

One or more embodiments of the invention comprise a steel strip that is thinner than the metal pipe and the test piece is in a state wrapped under tension around the outer peripheral face of the metal pipe and the test piece. Thus the steel strip is in a state in which damage such as by creep voids readily develops. Thus the degree of deterioration increases as the internal pressure creep test progresses, and along with usage of the metal pipe actual pipe). The steel strip is made of a metal material having a thermal expansion coefficient and strength of the metal pipe, or greater, thereby enabling a durability to be obtained that corresponds to the service life of the metal pipe and the test piece. A correlation can accordingly be acquired between the degree of deterioration of the steel strip and the remaining service life of the metal pipe and the test piece, thereby enabling the remaining service life of the metal pipe to be evaluated without scraping the surface of the metal pipe.

In the above remaining service life evaluation method, the steel strip is subjected to heat treatment in advance. In this method, deterioration of the steel strip is accelerated by the heat treatment, and so the progression in the degree of deterioration of the steel strip can be ascertained from immediately after installation to the metal pipe and the test piece.

In the above remaining service life evaluation method, the steel strip includes: a ring shaped section of a strip shaped thin metal sheet that is curved in a circular cylindrical shape and has a circumferential direction length determined so as to be shorter than a length around the outer peripheral face of the metal pipe; a pair of flange portions provided extending in an outer peripheral direction from circumferential direction ends of the ring shaped section; and a connection screw that adjusts a spacing between the flange portions and connects the flange portions with each other. In this method, the tension on the ring shaped section can be easily adjusted according to the degree of tightening (for example, the tightening torque) of the connection screw.

In the above remaining service life evaluation method, the steel strip is made of the same metal material as that of the metal pipe. In this method, the steel strip and the metal pipe are made of the same material, and so the remaining service life of the metal pipe can be evaluated with good precision.

According to one or more embodiments of the present invention, the remaining service life of a metal pipe suffering from creep damage can be measured without scraping the surface of the metal pipe.

DETAILED DESCRIPTION

Figure 1A:
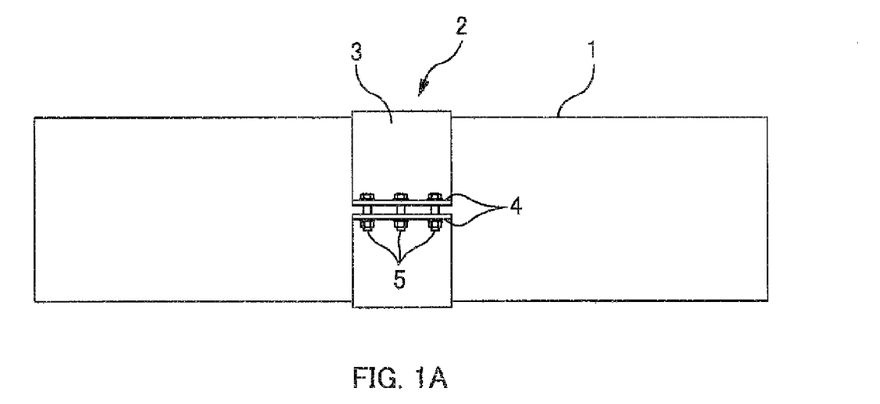
FIG. 1A is a plan view to explain a state in which a steel strip is wrapped around a boiler pipe.
Figure 1B:
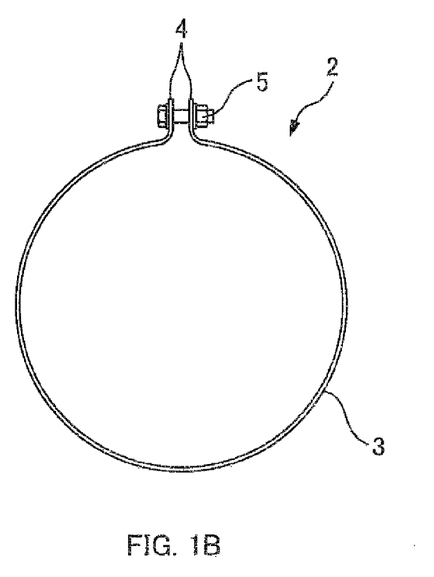
FIG. 1B is a diagram to explain a configuration of a steel strip.
Figure 1C:
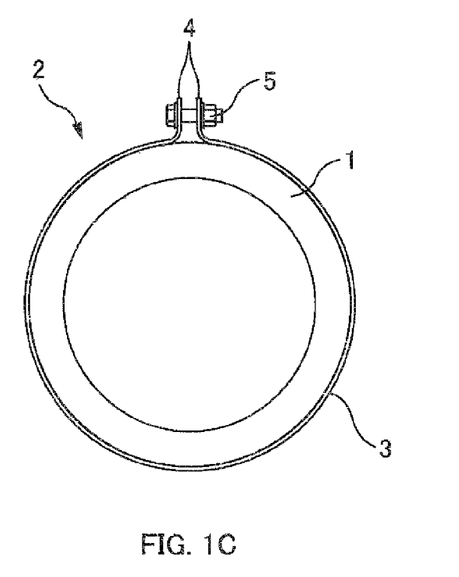
FIG. 1C is a cross-sectional view to explain a state in which a steel strip is wrapped around a boiler pipe.

Explanation follows regarding one or more embodiments of the present invention. Explanation first follows regarding a boiler pipe 1 subject to remaining service life evaluation, and a steel strip 2 wrapped around the boiler pipe 1, with reference to FIG. 1.

The boiler pipe 1 is a metal pipe of smaller diameter than a motive steam pipe, and is configured by a small diameter pipe having a diameter of from 30 mm to 100 mm, and a wall thickness of from 3 mm to 20 mm. The following may be applied as the material of the boiler pipe 1: a super stainless steel (for example, SUS312L), a stainless steel (for example, SUS304, SUS316), a high chromium steel (for example, 9 chrome steel, 12 chrome steel), a low chromium steel (for example, 1.0 chrome steel, 1.5 chrome steel, 2.25 chrome steel), and a carbon steel tube for boiler (STB). The temperature of fluid flowing through the boiler pipe 1 is, for example, within a range of from 250° C. to 650° C., and the steam pressure is, for example, within a range of from 2 MPa to 5 MPa.

The steel strip 2 is, as illustrated in FIG. 1A, in a state wrapped under tension around the outer peripheral face of the boiler pipe 1. The strength of the steel strip 2 is set so as to be the same as the boiler pipe 1, or greater than the boiler pipe 1. The steel strip 2 illustrated in FIG. 1B includes a ring shaped section 3, flange portions 4, and connection screws 5.

The ring shaped section 3 is a section formed by forming a strip shaped thin metal sheet into a circular cylindrical shape, and has a circumferential direction length determined so as to be slightly shorter than a length around the outer peripheral face of the metal pipe. A gap is thus formed running along the axial direction between one circumferential direction end and the other circumferential direction end of the ring shaped section 3 when the ring shaped section 3 is wrapped around the outer peripheral face of the boiler pipe 1.

The ring shaped section 3 is manufactured from a metal material having a thermal expansion coefficient and a strength of the metal pipe, or greater. Specifically, the metal material is selectable from a stainless steel (for example, SUS304, SUS316), a high chromium steel (for example, 9 chrome steel, 12 chrome steel), a low chromium steel (for example, 1.0 chrome steel, 1.5 chrome steel, 2.25 chrome steel), or the like. The thickness of the ring shaped section 3 is thin enough so as not to have a great impact on the strength of the boiler pipe 1; and is, for example, determined so as to be a thickness of about from 0.1 mm to 1.0 mm. With regards to the metal material configuring the ring shaped section 3 (the steel strip 2), as stated above, it is sufficient for the metal material to have a thermal expansion coefficient and a strength of the boiler pipe 1, or greater; however, the same material as the boiler pipe 1 is employed.

The flange portions 4 are rectangular shaped portions provided extending out in an outer peripheral direction from the circumferential direction ends of the ring shaped section 3, and are manufactured from the same material as the ring shaped section 3. The flange portions 4 are provided as a pair at the circumferential direction ends of the ring shaped section 3, and are joined to the ring shaped section 3 by welding.

The connection screws 5 are members that adjust the spacing between the flange portions 4, and connect the flange portions 4 with each other. The connection screws 5 are configured by pairs of bolts and nuts, and are manufactured from the same material as the steel strip 2.

As illustrated in FIG. 1C, the spacing between the flange portions 4 changes as the connection screws 5 are tightened or loosened in a state in which the steel strip 2 has been wrapped around the outer peripheral face of the boiler pipe 1, and the tension of the ring shaped section 3 (the tightening force on the metal pipe) is thereby adjusted. The tension of the ring shaped section 3 and the tightening torque of the connection screws 5 are correlated to each other, enabling the tension of the ring shaped section 3 to be set based on the tightening torque.

Next, explanation follows regarding employing the steel strip 2 to evaluate the remaining service life of the boiler pipe 1 (metal pipe). The remaining service life evaluation of the present embodiment includes, broadly speaking, two processes. The first process is master curve preparation processing, and the second process is remaining service life evaluation processing performed on site. Explanation follows regarding each process. In the following explanation, the steel strip 2 employed is of the same material as the boiler pipe 1 (for example, SUS304, or 9 chrome steel).

Figure 2A:
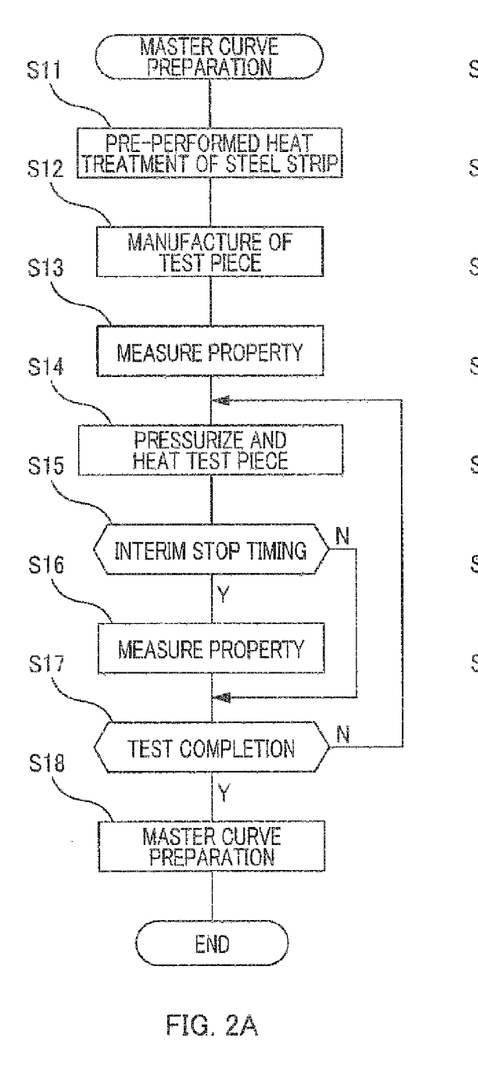
FIG. 2A is a flowchart of master curve preparation processing.

First, explanation follows regarding master curve preparation processing. As illustrated in FIG. 2A, heat treatment is performed in advance on the steel strip 2 in this preparation processing (S11). For example, the steel strip 2 is placed in a furnace set to a temperature that is from 20° C. to 50° C. higher than the actual temperature of use, and is heated for a specific duration. The service life of the steel strip 2 is consumed by the heating, and a change in state (deterioration) is liable to occur due to creep damage.

For example, creep voids are liable to develop when the steel strip 2 is manufactured from stainless steel. Moreover, coarse granulation and fine granulation develop when the steel strip 2 is manufactured from chromium steel. The heating duration of the heat treatment performed in advance is set, for example, such that a usage time is set to allow the remaining service life of the steel strip 2 ((creep rupture time−usage time)/creep rupture time)) to be 0.5.

Figure 3:
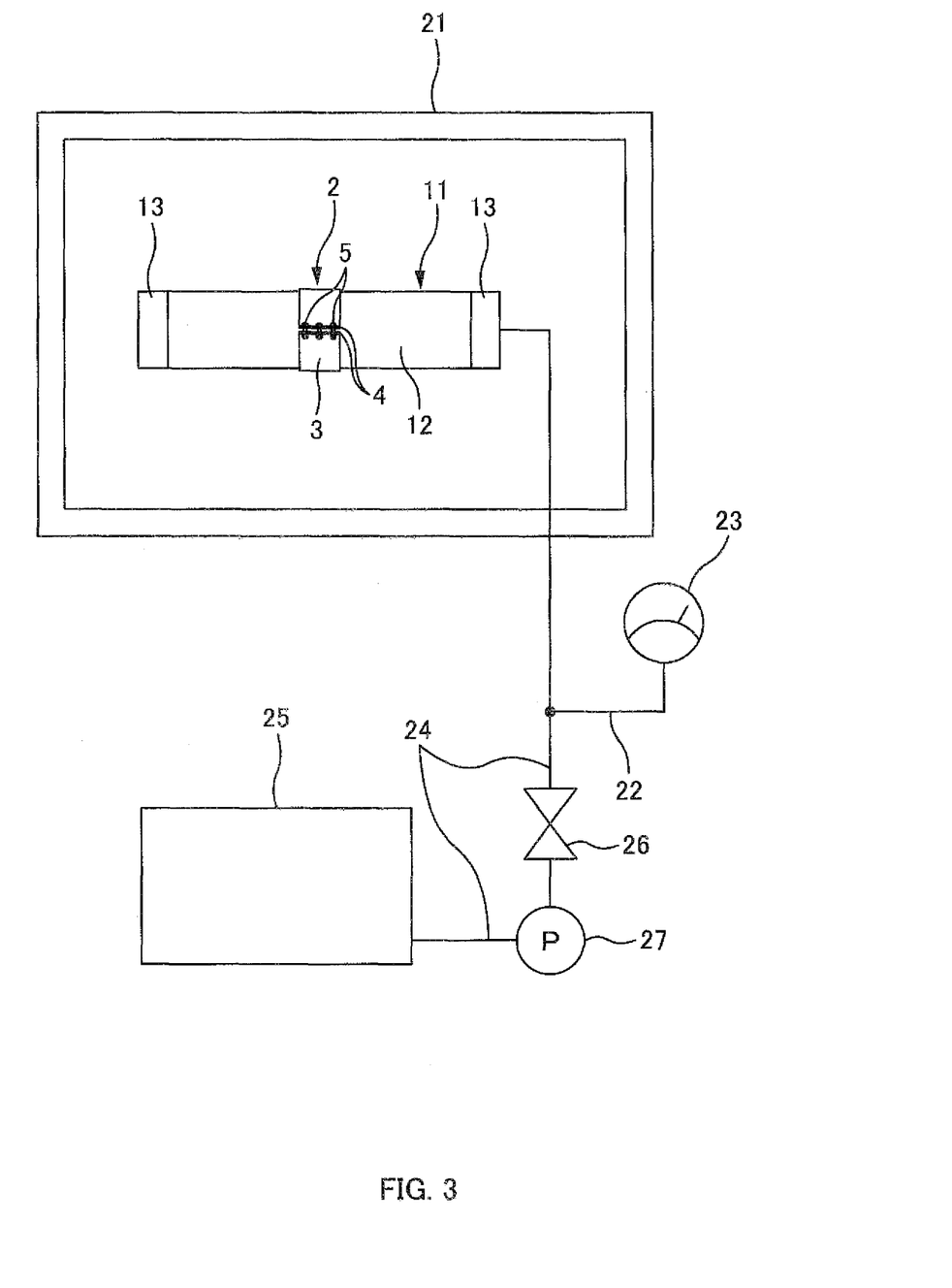
FIG. 3 is a schematic explanatory diagram of a test device for an internal pressure creep test.

Next, manufacture of a test piece 11 is performed (S12). In this step, the test piece 11 illustrated in FIG. 3 is manufactured. The test piece 11 includes a short pipe 12, plugs 13, and a conduit 24. The short pipe 12 is a short (for example, 200 mm to 300 mm) metal pipe made from the same material and having the same inner and outer diameters as the boiler pipe 1 subject to remaining service life evaluation. The plugs 13 are metal circular plug members to be welded onto each of the two ends of the short pipe 12. The plugs 13 are also manufactured from the same material as the boiler pipe 1. A through hole (not illustrated in the drawings) is formed in one of the plugs 13 so as to pass through along the thickness direction of the plug 13. The conduit 24 is a metal pipe in a state of air-tight communication with the internal space of the test piece 11. One end of the conduit 24 is welded to one of the plugs 13 so as to be in communication with the through hole.

The steel strip 2 is wrapped around the outer peripheral face of the test piece 11. When this is performed, the tension of the ring shaped section 3 is adjustable by the degree of tightening of the connection screws 5. In the present embodiment, the tension of the ring shaped section 3 is adjusted so as to give a tightening force larger than the pressure of fluid (steam) to be flowed through the boiler pipe 1 (the metal pipe). For example, if the pressure of fluid flowing in the boiler pipe 1 is 40 MPa, then the tension of the ring shaped section 3 is adjusted such that the tightening force from the ring shaped section 3 is from 50 MPa (1.2 times) to 80 MPa (2 times).

At the time the steel strip 2 is attached, initial property measurements are performed, as illustrated in FIG. 2A (S13). At this step, a property (degree of deterioration) of the steel strip 2 is measured immediately prior to performing an internal pressure creep test. The property of the steel strip 2 to be measured here is determined by remaining service life evaluation method. For example, when employing a hardness test method, the hardness of the steel strip 2 is measured. Moreover, when employing an M parameter method, the maximum creep void grain boundary occupancy is measured. Similarly, when employing an A parameter method, the A parameter (number of grain boundaries where voids develop/total number of grain boundaries observed) is measured.

Other examples of evaluation methods include a void surface area ratio method, a void number density method, an L parameter method, and a magnetic method. The corresponding property is measured when employing each of these evaluation methods. In the following explanation an example is given of a case in which evaluation is performed using an M parameter method.

An internal pressure creep test is performed after initial property measurements have been performed.

In the internal pressure creep test, first the test piece 11 is pressurized and heated (S14). For example, as illustrated in FIG. 3, the test piece 11 is placed inside a heating furnace 21, with a pressure gauge 23 connected to a section of a conduit 22 outside the furnace. The conduit 24 branches off outside the furnace, and is connected to a water tank 25. A valve 26 and a pump 27 are installed partway along the branched conduit 24. The test piece 11 is heated inside the heating furnace 21, and is fed with water by operating the pump 27. This water becomes steam, raising the internal pressure of the test piece 11. The test piece 11 is pressurized and heated, while adjusting the internal pressure of the test piece 11 using the water feed. For example, the test piece 11 is pressurized and heated under conditions of 40 MPa and 600° C.

In the present embodiment, a metal sheet that is thinner than the short pipe 12 configuring the test piece 11 is employed for the steel strip 2, and wrapped around the short pipe 12 in a tensioned state. Thus creep voids develop in the steel strip 2 earlier than in the short pipe 12, and the creep voids readily increase on pressurizing and heating. Further, the speed of increase in the creep voids can also be adjusted by the tension imparted to the steel strip 2. Moreover, in the present embodiment, due to the heat processing that has been performed in advance on the steel strip 2, creep voids can be confirmed from the initial stage of the test.

Next, as illustrated in FIG. 2A, determination is made as to whether or not an interim stop timing has been reached (15). The interim stop timing here corresponds to a timing for measurement of the state of damage. It has been found from experience that damage progression becomes more significant as the remaining service life gets shorter. Thus the interim stop timings are set so as to be spaced at shorter intervals as the test duration gets longer. Processing transitions to interim property measurement (S16) when an interim stop timing has been reached, and processing transitions to test completion determination (S17) when an interim stop timing has not been reached.

In an interim property measurement (S16), pressurizing and heating of the test piece 11 is temporarily stopped and the property of the steel strip 2 is measured. The property measurement is performed here in a similar manner to the initial property measurement at step S13. Since evaluation is performed by an M parameter method in the present embodiment, the maximum creep void grain boundary occupancy is measured. When property measurement has been completed, the post-measurement steel strip 2 is re-wrapped around the test piece 11 with the same tension. Processing then transitions to test completion determination (S17).

At test completion determination (S17), determination is made as to whether or not the internal pressure creep test has been completed. Whether or not the test has been completed is determined here based on whether or not the test piece 11 has ruptured. Namely, test completion (Y) is determined when the test piece 11 has ruptured, and test continuation (N) is determined when the test piece 11 has not ruptured.

Figure 4A:
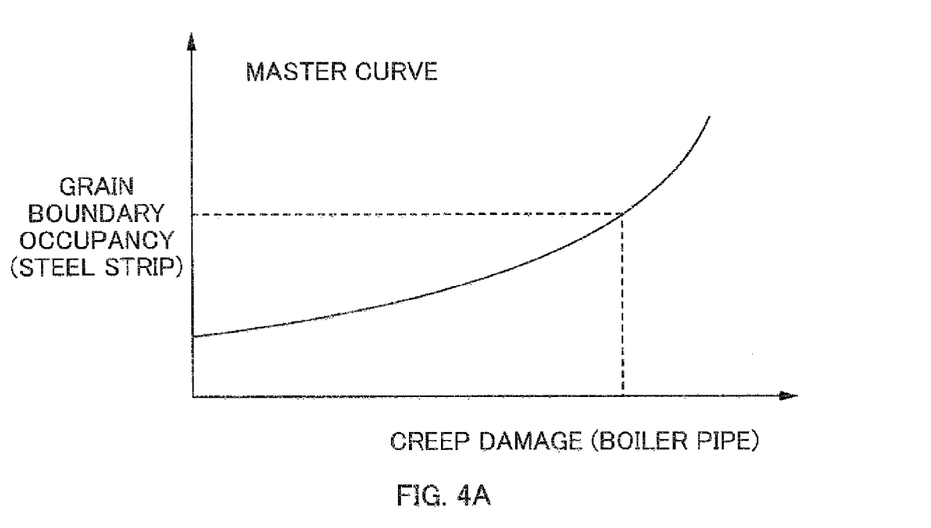
FIG. 4A is a diagram illustrating an example of a master curve corresponding to a new boiler pipe.

Master curve preparation (S18) is performed when test completion has been determined. A master curve is prepared here expressing a relationship between creep damage to the test piece 11 (the boiler pipe 1) and the degree of deterioration of the steel strip 2. In the example of FIG. 4A, creep damage is set as the horizontal axis, and the maximum creep void grain boundary occupancy is set as the vertical axis. The maximum value of creep damage is at rupture (end of service life of the pipe), and hence the horizontal axis gives an indication of the remaining service life until rupture. One sequence of processing is completed by the preparation of the master curve.

Figure 4B:
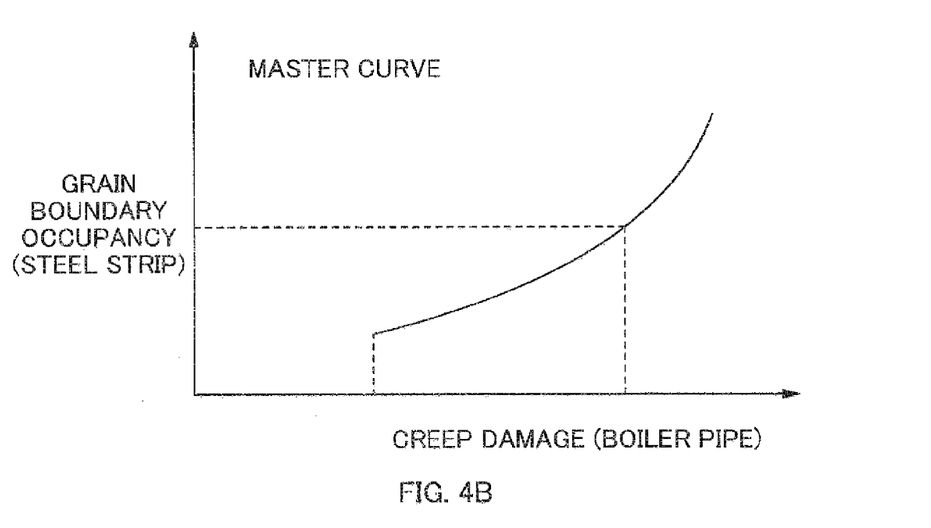
FIG. 4B is a diagram illustrating an example of a master curve corresponding to an in-use boiler pipe.

Explanation has been given in the example of FIG. 4A of a case in which the steel strip 2 is attached from the start of the internal pressure creep test; however, there is no limitation to this example. For example, the steel strip 2 may be attached to the test piece 11 after a stipulated duration has elapsed from the start of internal pressure creep test. In such cases, as illustrated in FIG. 4B, the degree of deterioration of the steel strip 2 is acquired from the point in time when creep damage has already progressed in the test piece 11. The remaining service life evaluation may be performed for the in-use boiler pipe 1 by preparing such master curves.

Figure 2B:
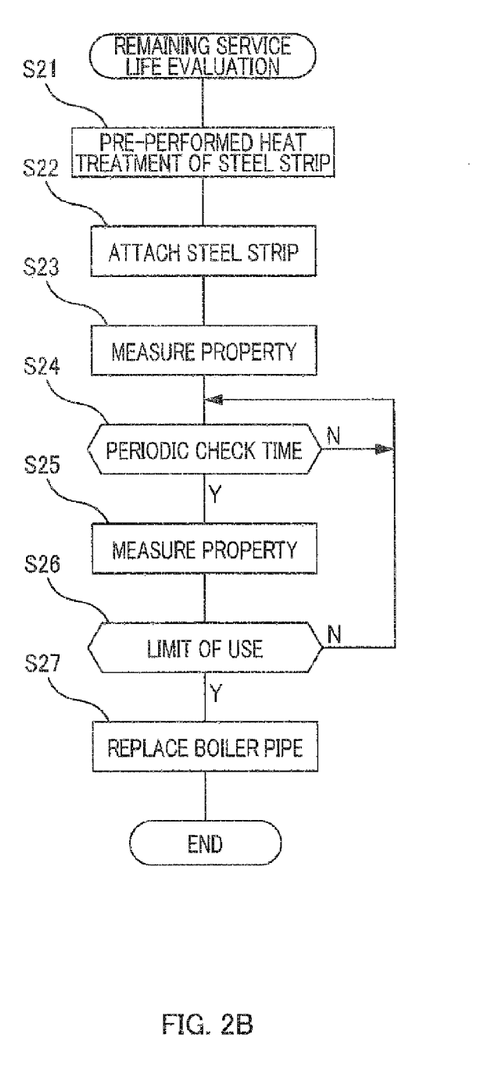
FIG. 2B is a flowchart of remaining service life evaluation processing.

Next, explanation follows regarding on-site remaining service life evaluation processing. As illustrated in FIG. 2B, heat treatment (S21) is performed in advance on the steel strip 2 in this evaluation processing. The heat treatment is performed in advance here under the same conditions as those during the master curve preparation. Processing to attach the steel strip 2 (S22) is performed subsequently to the heat treatment performed in advance. For example, the steel strip 2 is attached to a new boiler pipe 1 when replacement is performed. The degree of tightening of the connection screws 5 is adjusted when attaching the steel strip 2, and the same tension is imparted as during master curve preparation. Note that when attaching the steel strip 2 to an in-use boiler pipe 1, the steel strip 2 is attached at the point in time when the duration of use of the boiler pipe 1 has reached a stipulated time of the master curve preparation time.

Initial property measurement (S23) is performed at the time when the steel strip 2 is attached. At this step, the property (degree of deterioration) of the steel strip 2 is measured directly after attachment. Similarly to during master curve preparation, the property of the steel strip 2 to be measured here is also determined by remaining service life evaluation method. Since an M parameter method is employed in the present embodiment, the maximum creep void grain boundary occupancy is measured.

Determination is then made as to whether or not it is time to perform a periodic check (S24). The property of the steel strip 2 is measured (S25) when the time for a periodic check has arrived, and evaluation is made as to whether or not a limit of use has been reached (S26). For example, during periodic checks, the maximum creep void grain boundary occupancy is measured for the steel strip 2 (the ring shaped section 3), and applied to the master curve to find the remaining service life (creep damage). Whether or not the limit of use will be reached before the next periodic check is evaluated from the remaining service life found. Replacement of the boiler pipe 1 is performed (S27) when evaluated to be at the limit of use. On the other hand, when not evaluated to be at the limit of use, the post-measurement steel strip 2 is re-wrapped around the boiler pipe 1 with the same tension, and is left in place until the next periodic check time (S24).

As explained above, according to the remaining service life evaluation method of the present embodiment, the steel strip 2 that is thinner than the boiler pipe 1 (metal pipe) and the test piece 11 is in a state wrapped under tension around the outer peripheral face of the boiler pipe 1 and the test piece 11, and so the steel strip 2 is in a state in which damage, such as by creep voids, readily develops. Thus, the degree of deterioration increases as the internal pressure creep test progresses, and with usage of the boiler pipe 1. The steel strip 2 is manufactured from a metal material having a thermal expansion coefficient and strength of the boiler pipe 1 and the test piece 11, or greater, thereby enabling a durability to be obtained according to the service life of the boiler pipe 1 and the test piece 11. A correlation, between the degree of deterioration of the steel strip 2 and the remaining service life of the boiler pipe 1 and the test piece 11, can accordingly be acquired, thereby enabling the remaining service life of the boiler pipe 1 to be evaluated without scraping the surface of the boiler pipe 1.

Moreover, the steel strip 2 is subjected to heat treatment in advance and deterioration is accelerated, thus the progression in the degree of deterioration of the steel strip 2 can be ascertained immediately after installation to the boiler pipe 1 and the test piece 11. The steel strip 2 is manufactured from the same metal material as the boiler pipe 1, enabling the remaining service life of the boiler pipe 1 to be evaluated with good precision.

Moreover, the steel strip 2 is a strip shaped thin metal sheet curved in a circular cylindrical shape, and includes: the ring shaped section 3 with a circumferential direction length determined so as to be shorter than the length around the outer peripheral face of the boiler pipe 1; the pair of flange portions 4 provided extending in an outer peripheral direction from the circumferential direction ends of the ring shaped section 3; and the connection screws 5 that adjust the spacing between the flange portions 4 and connect the flange portions 4 with each other. Thus the tension of the ring shaped section 3 can be easily adjusted according to the tightening torque on the connection screws 5.

The above explanation of the embodiment is to facilitate understanding of the present invention, and does not limit the present invention. The present invention may be modified and improved without departing from the gist thereof, and the invention includes equivalents thereof. For example, the following configurations may be employed.

Although in the above embodiment the service life of the steel strip 2 is pre-consumed by performing the heat treatment in advance, the method is not limited thereto. For example, a steel strip 2 that is not subjected to heat treatment in advance may be employed.

Although in the above embodiment a configuration is adopted in which the pair of flange portions 4 are provided at the two ends of the ring shaped section 3, such that the spacing between the flange portions 4 is adjusted by the connection screws 5, another configuration may be adopted, as long as the tension of the ring shaped section 3 is adjustable.

Moreover, although the boiler pipe 1 has been given as an example of a metal pipe, the present invention may be similarly applied even for a large diameter pipe employed for motive steam.

REFERENCE SIGNS LIST

1 . . . boiler pipe, 2 . . . steel strip, 3 . . . ring shaped section, 4 . . . flange portion, 5 . . . connection screw, 11 . . . test piece, 12 . . . short pipe, 13 . . . plug, 14 . . . conduit, 21 . . . heating furnace, 22 . . . conduit, 23 . . . pressure gauge, 24 . . . conduit, 25 . . . water tank, 26 . . . valve, 27 . . . pump Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

The invention claimed is:

1. A remaining service life evaluation method for evaluating a remaining service life of a metal pipe suffering from creep damage on a basis of a master curve that is prepared in advance, the master curve being prepared by performing an internal pressure creep test in a state in which a steel strip, made of a metal material having a thermal expansion coefficient and strength of the metal pipe or greater, is wrapped under tension around an outer peripheral face of a test piece made of the same material and having the same inner and outer diameters as the metal pipe, the master curve indicating a relationship between a degree of deterioration of the steel strip and a remaining service life of the metal pipe, the remaining service life evaluation method comprising:
    wrapping a steel strip around an outer peripheral face of the metal pipe under the same conditions as those during the internal pressure creep test; and
    evaluating a remaining service life of the metal pipe on a basis of a degree of deterioration of the steel strip.

2. The remaining service life evaluation method according to claim 1, wherein the steel strip is subjected to heat treatment in advance.

3. The remaining service life evaluation method according to claim 1, wherein the steel strip includes:
    a ring shaped section of a strip shaped thin metal sheet that is curved in a circular cylindrical shape and has a circumferential direction length determined so as to be shorter than a length around the outer peripheral face of the metal pipe;
    a pair of flange portions provided extending in an outer peripheral direction from circumferential direction ends of the ring shaped section; and
    a connection screw that adjusts a spacing between the flange portions and connects the flange portions with each other.

4. The remaining service life evaluation method according to claim 2, wherein the steel strip includes:
    a ring shaped section of a strip shaped thin metal sheet that is curved in a circular cylindrical shape and has a circumferential direction length determined so as to be shorter than a length around the outer peripheral face of the metal pipe;

a pair of flange portions provided extending in an outer peripheral direction from circumferential direction ends of the ring shaped section; and a connection screw that adjusts a spacing between the flange portions and connects the flange portions with each other.

5. The remaining service life evaluation method according to claim 1, wherein the steel strip is made of the same metal material as that of the metal pipe.

6. The remaining service life evaluation method according to claim 2, wherein the steel strip is made of the same metal material as that of the metal pipe.

7. The remaining service life evaluation method according to claim 3, wherein the steel strip is made of the same metal material as that of the metal pipe.

8. The remaining service life evaluation method according to claim 4, wherein the steel strip is made of the same metal material as that of the metal pipe.

* * * * *